(12) United States Patent
Orritt et al.

(10) Patent No.: US 9,480,436 B1
(45) Date of Patent: Nov. 1, 2016

(54) PROBE HOUSING ASSEMBLY

(75) Inventors: Chris Orritt, Wigan (GB); Richard Joshi, Wigan (GB)

(73) Assignee: ATG R&D LIMITED, Wigan (GB)

( * ) Notice: Subject to any disclaimer, the term of this patent is extended or adjusted under 35 U.S.C. 154(b) by 749 days.

(21) Appl. No.: 13/525,138

(22) Filed: Jun. 15, 2012

Related U.S. Application Data

(60) Provisional application No. 61/504,132, filed on Jul. 1, 2011.

(51) Int. Cl.
*A61N 5/10* (2006.01)
*A61B 6/00* (2006.01)

(52) U.S. Cl.
CPC .. *A61B 6/00* (2013.01); *A61N 5/10* (2013.01)

(58) Field of Classification Search
CPC ............................ A61N 5/1014; A61B 6/4258
USPC ....................................................... 250/505.1
See application file for complete search history.

(56) References Cited

U.S. PATENT DOCUMENTS

| | | | |
|---|---|---|---|
| 3,574,981 A * | 4/1971 | Henschen | 52/127.2 |
| 2001/0049528 A1* | 12/2001 | Kubota | 606/65 |
| 2005/0051559 A1* | 3/2005 | Yamashita | 220/366.1 |
| 2009/0211750 A1* | 8/2009 | Toporowski et al. | 166/84.1 |
| 2010/0001239 A1* | 1/2010 | Dufour | 254/100 |

* cited by examiner

*Primary Examiner* — Robert Kim
*Assistant Examiner* — Sean Luck
(74) *Attorney, Agent, or Firm* — Ronald J Koch

(57) ABSTRACT

A novel probe housing assembly comprises a body, a cap, and a retainer. The retainer is adapted to releasably engage the body and the cap wherein, a second edge of the cap abuts a first edge of the body, and a third threaded portion of the retainer engages, by five complete revolutions, a second threaded portion of the cap, and a third threaded portion of the retainer engages, by five complete revolutions, the first threaded portion of the body whereby the cap is releasably secured to the body by the retainer thus achieving an EX-D compliant seal.

1 Claim, 5 Drawing Sheets

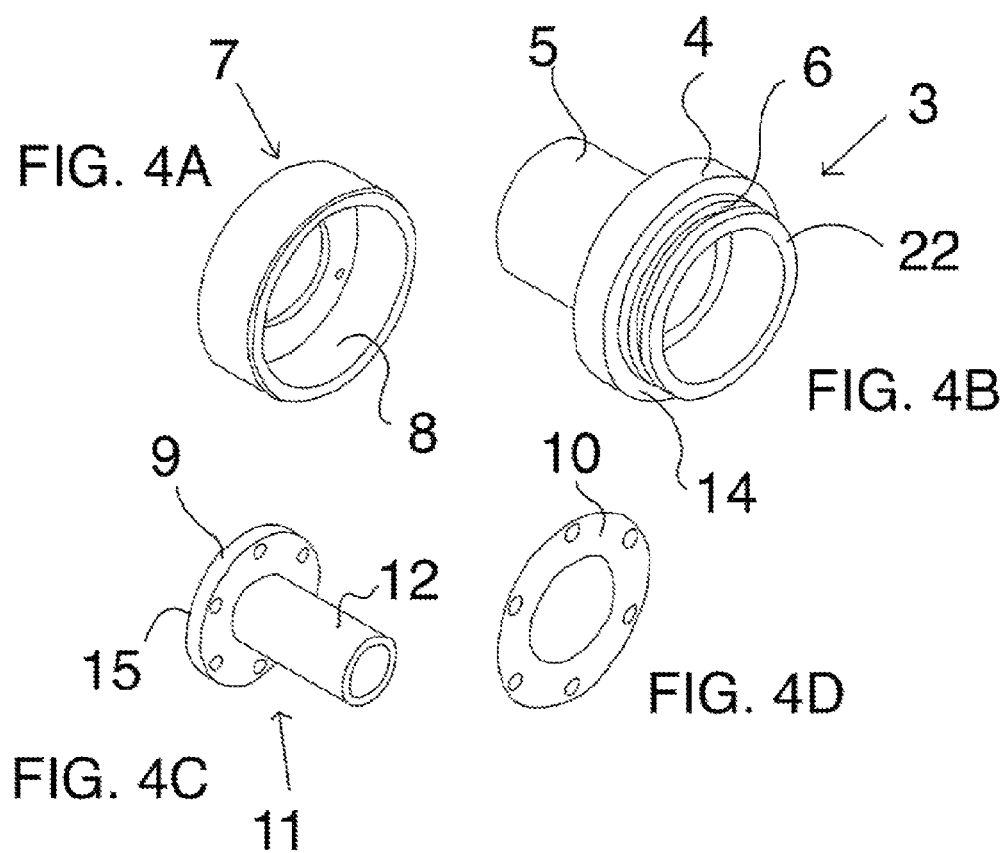

PROBE HOUSING ASSEMBLY

The present application is related to the provisional patent application No. 61/504,132 of Richard Joshi et al, filed Jul. 1, 2011, entitled "Probe Housing Assembly", and based on which priority is herewith claimed under 35 U.S.C. 119(e) and the disclosure of which is incorporated herein by reference in its entirety as if fully rewritten herein.

BACKGROUND AND SUMMARY

The present invention relates generally to UV treatment systems and specifically to systems and methods for achieving flame restrictive seals in such systems. To achieve EX-D compliance, conventional systems require large enclosures be used to house and connect various components (e.g. UV probes) to UV treatment reactors. The present invention allows a smaller enclosure to be used by providing a single retainer that engages the threaded portions of a body and cap. The threaded portions thereof having sufficient thread pitch and length to achieve a compliant flame path.

BRIEF DESCRIPTION OF THE DRAWINGS

FIG. 4A depicts a perspective view of retainer 7.
FIG. 4B depicts a perspective view of cap 3.
FIG. 4C depicts a perspective view of tube 11.
FIG. 4D depicts a perspective view of gasket 10.

DETAILED DESCRIPTION

Figure 1:
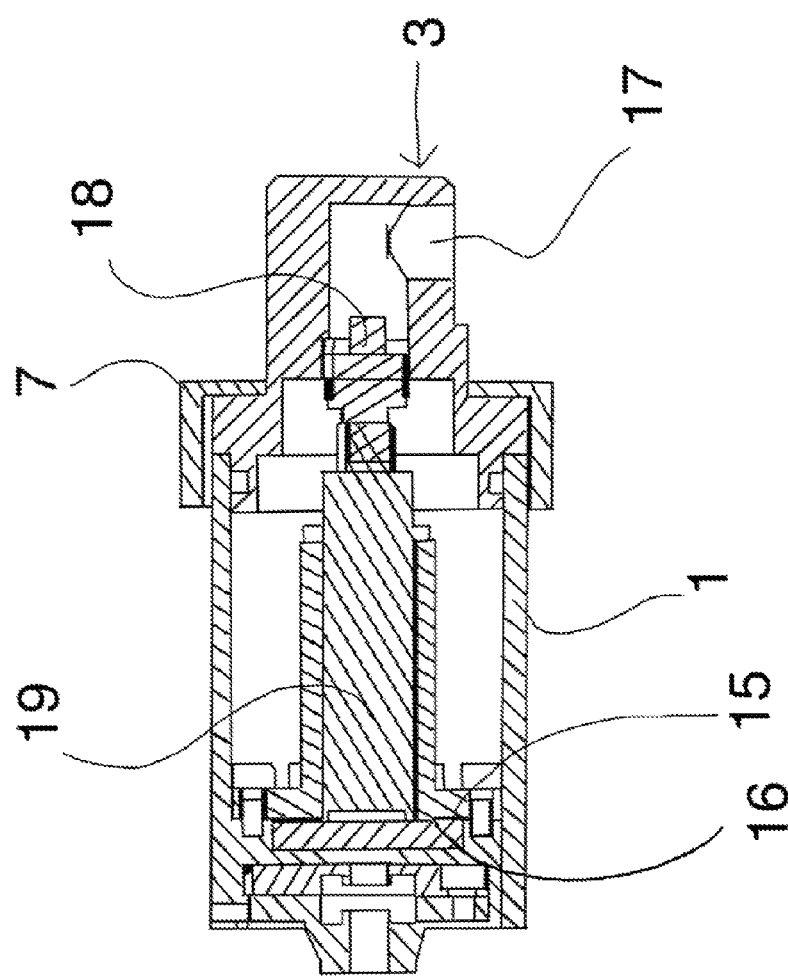
FIG. 1 depicts a cross sectional side view of the invention.
Figure 2:
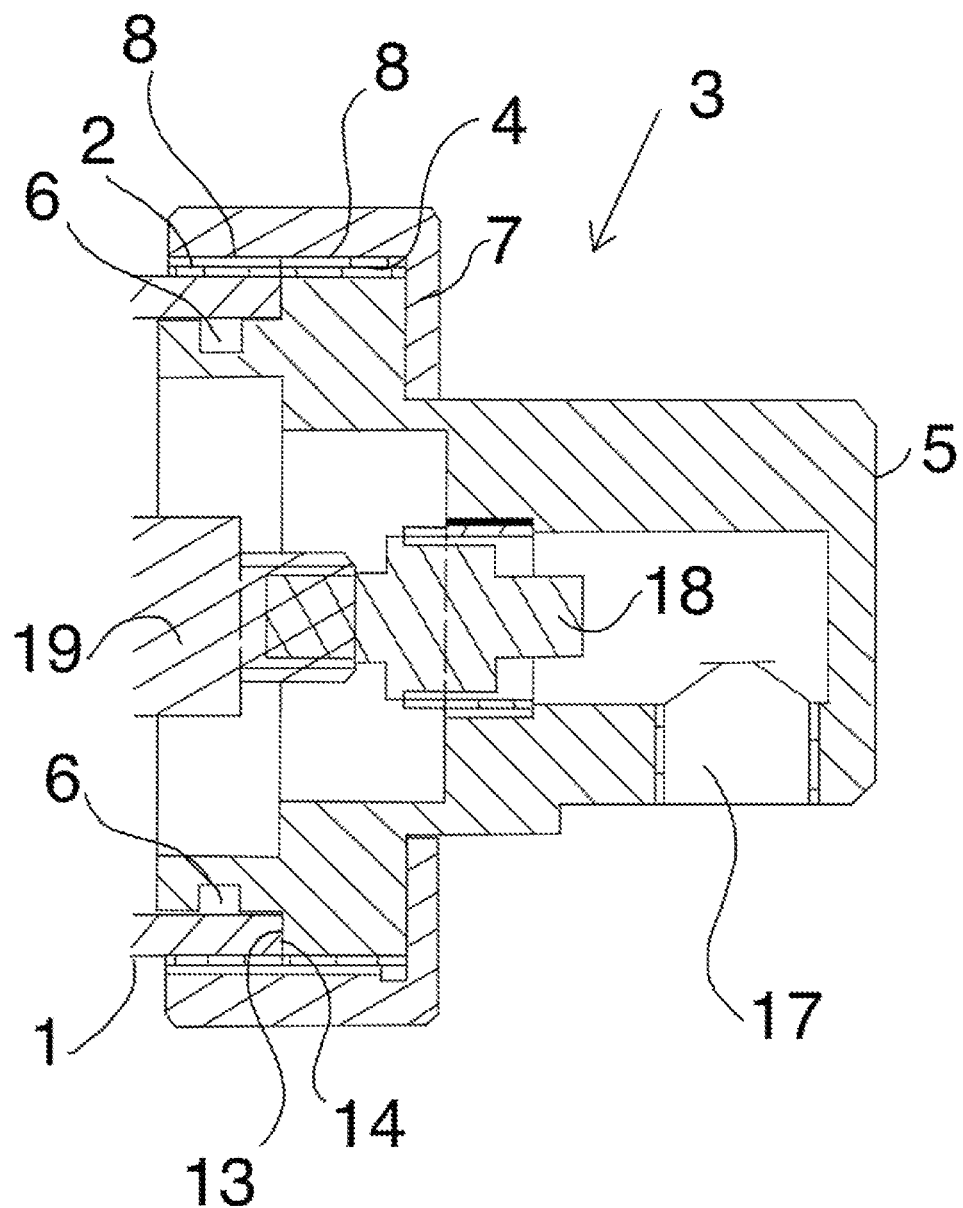
FIG. 2 depicts an enlarged cross sectional view thereof.
Figure 3:
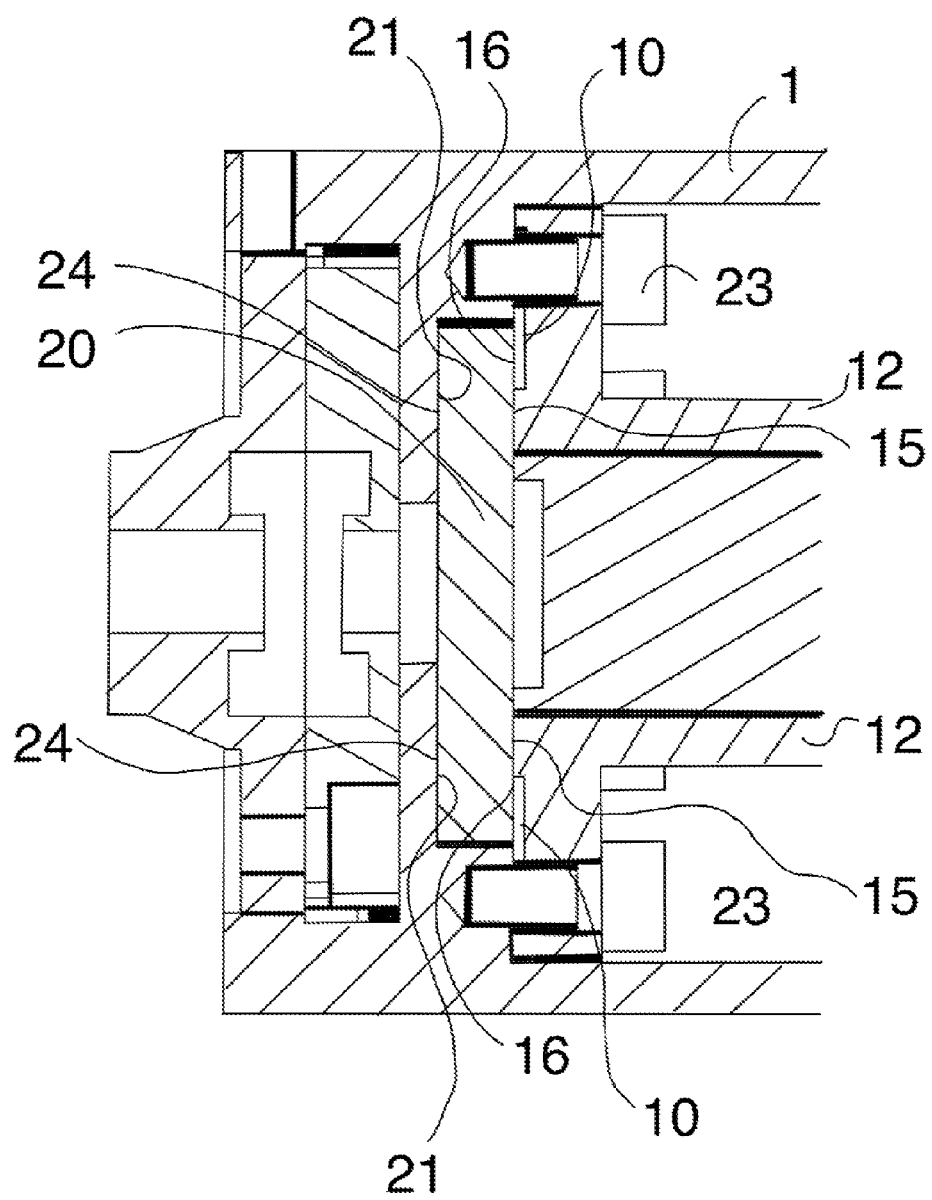
FIG. 3 depicts a second enlarged cross sectional view thereof.
Figure 5A:
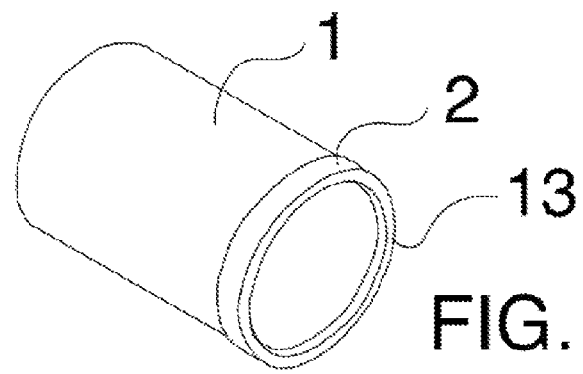
FIG. 5A depicts a perspective view of body 1.
Figure 5B:
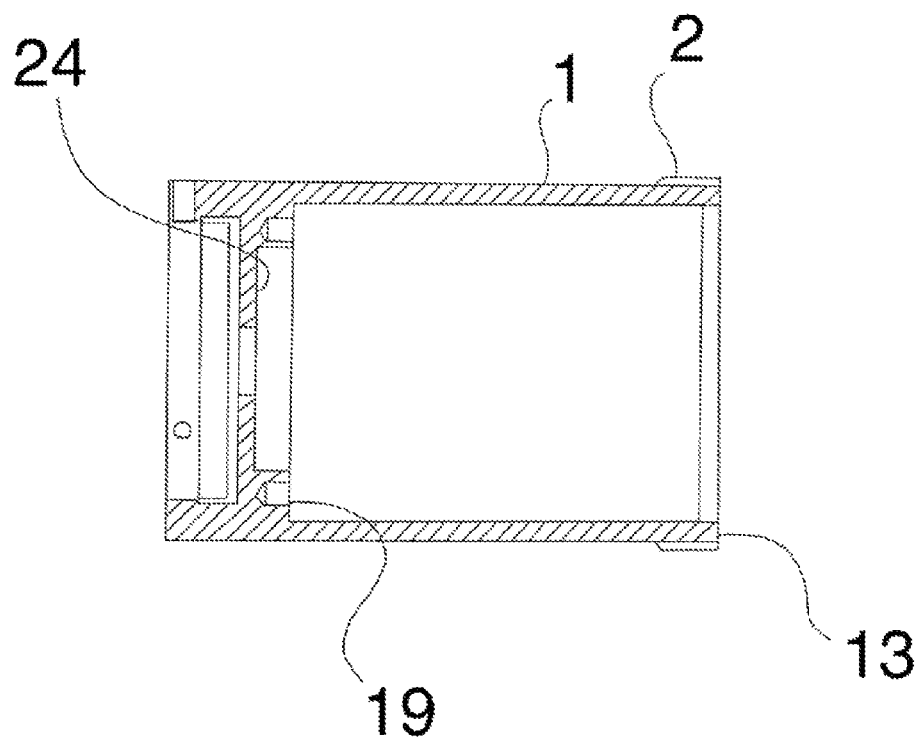
FIG. 5B depicts a cross sectional side view of body 1.

One embodiment of a Probe Housing Assembly comprises Body 1, tube 11, gasket 10, cap 3, quartz window 20, and retainer 7 and is adapted such that probe 19 fits within sleeve portion 12.

Body 1 comprises first threaded portion 2, first edge 13, and fourth edge 24. Cap 3 comprises proximal portion 22 having therein groove 6 (for placement of an o-ring therein), distal portion 5, second threaded portion 4, second edge 14, and aperture 17 in distal portion 5.

Retainer 7 has third threaded portion 8. Tube 11 comprises flange 9, sleeve portion 12, and third edge 15. Quartz window 20 has inner and outer surfaces 16 & 21, respectively. Gasket 10 is 1.5 millimeters thick uncompressed and 1 millimeter thick compressed.

Probe 19 is operatively connected with wires (not shown) to probe connector 18 via aperture 17 in distal portion 5 of cap 3 in conjunction with a standard ATEX cable gland.

Quartz window 20 is substantially disk shaped having a 40 millimeter diameter and 6 millimeter thickness and fitting between fourth edge 24 of body 1 and third edge 15 of tube 11. Gasket 10 fits between inner surface 16 of quartz window 20 and third edge 15 of tube 11. Tube retaining screws 23 releasably secure tube 11 to body 1.

Retainer 7 releasably secures cap 3 to body 1 wherein, second edge 14 of cap 3 abuts first edge 13 of body 1; and third threaded portion 8 of retainer 7 engages second threaded portion 4 of cap 3 and first threaded portion 2 of body 1. Each of threaded first portion 2 of body 1 and second threaded portion 4 of cap 3 have a 1.5 millimeter pitch and require 5 complete revolutions of retainer 7 to exceed minimum EX-D requirements.

Flame paths are identified between outer surface 21 of quartz window 20 and fourth edge 24 of body 1 and then between either or both of third edge 15 of tube 11 and inner surface 16 of quartz window 20 or through the threaded aperture for tube retaining screws 23. The 40 millimeter diameter of quartz window 20 exceeds the necessary 12.5 millimeter minimum EX-D requirement.

Flame paths are identified between second edge 14 of cap 3 and first edge 13 of body 1 and then between either or both of third threaded portion 8 of retainer 7 and second threaded portion 4 of cap 3 or between third threaded portion 8 of retainer 7 and first threaded portion 2 of body 1 thereby achieving a distinct advantage of the present invention by providing an EX-D compliant seal. This dual-threaded method and structure allows a smaller enclosure to be used. Conventional systems and methods require a larger enclosure be used to house probe 19 and tube 11.

What is claimed is:
1. A novel probe housing assembly comprising:
a body, a cap, and a retainer;
the body having an outer diameter of 66 mm, and further comprising,
    a first threaded portion having a 1.5 mm pitch, a first edge, and a fourth edge;
the cap comprising,
    a second threaded portion having a 1.5 mm pitch, and a second edge;
the retainer adapted to releasably engage the body and the cap, and further having a third threaded portion with a 1.5 mm pitch;
wherein, the second edge of the cap abuts the first edge of the body;
further wherein the third threaded portion of the retainer engages, by five complete revolutions, the second threaded portion of the cap;
further wherein the third threaded portion of the retainer engages, by five complete revolutions, the first threaded portion of the body;
whereby the cap is releasably secured to the body by the retainer.

* * * * *